(12) United States Patent
Ellison et al.

(10) Patent No.: US 10,288,572 B2
(45) Date of Patent: May 14, 2019

(54) APPARATUS FOR DESTRUCTIVE EVENT TESTING OF CHEMICAL ENERGY SYSTEMS USING HIGHLY PORTABLE AND EASE OF ACCESS ADAPTIVE HEAT FLOW TESTING SYSTEMS INCLUDING REPLACEABLE AND THERMALLY ISOLATED MODULAR THERMAL SECTIONS EACH CAPABLE OF INDEPENDENT MEASUREMENTS OF A TEST ARTICLE WITH IMPROVED EASE OF TEST ARTICLE INSERTION AND REMOVAL AND RELATED METHODS

(71) Applicant: The United States of America as represented by the SEC of the Navy, Washington, DC (US)

(72) Inventors: Daniel Ellison, Odon, IN (US); Ryan Ubelhor, Solsberry, IN (US); Cecilia Pierce, Bedford, IN (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 15/669,522

(22) Filed: Aug. 4, 2017

(65) Prior Publication Data
US 2018/0143149 A1 May 24, 2018

Related U.S. Application Data

(63) Continuation-in-part of application No. 15/226,604, filed on Aug. 2, 2016, which is a continuation-in-part
(Continued)

(51) Int. Cl.
*G01N 25/32* (2006.01)
*G01K 17/08* (2006.01)
(Continued)

(52) U.S. Cl.
CPC ............. *G01N 25/32* (2013.01); *G01K 17/00* (2013.01); *G01K 17/08* (2013.01); *G01N 25/20* (2013.01)

(58) Field of Classification Search
CPC ......... G01K 19/00; G01K 17/00; G01N 25/20
(Continued)

(56) References Cited

U.S. PATENT DOCUMENTS

| | | | | |
|---|---|---|---|---|
| 4,859,077 A | * | 8/1989 | Ito ..................... | G01N 25/4846 374/33 |
| 4,892,707 A | * | 1/1990 | Stockton ............. | B01J 19/0006 374/31 |

(Continued)

*Primary Examiner* — Nathaniel T Woodward
(74) *Attorney, Agent, or Firm* — Christopher A. Monsey

(57) ABSTRACT

Apparatus and methods are provided for providing flexible and repairable testing capabilities, including destructive testing, for systems that generate or absorb heat such as energy storage systems. One embodiment can include a heat exchange system adapted to contain and maintain a fluid at a predetermined temperature, thermally conductive tubing in direct intimate contact with a plurality of heat sinks, thermal sensor assemblies, and an sample vessel receiver structure where the thermal sensor assemblies, heat sinks removeably attach to different sections of the inner containment structure so as to measure heat flow into or out of the inner containment structure's different sections, and a test cell enclosure which is adapted to contain forces and output from destructive testing of samples. Embodiments of the disclosure enable rapid insertion/removal of samples as well as replacement of sections of the system including thermal sensor assemblies as well as enabling separate thermal measurements associated with different sections of a sample under test.

15 Claims, 11 Drawing Sheets

Related U.S. Application Data of application No. 14/539,241, filed on Nov. 12, 2014, now Pat. No. 9,739,670.

(60) Provisional application No. 62/200,535, filed on Aug. 3, 2015, provisional application No. 62/035,738, filed on Aug. 11, 2014.

(51) Int. Cl.
*G01N 25/20* (2006.01)
*G01K 17/00* (2006.01)

(58) Field of Classification Search
USPC ............... 374/1, 2, 3, 4, 5, 31, 33, 34, 208; 702/127, 130, 136
See application file for complete search history.

(56) References Cited

U.S. PATENT DOCUMENTS

| | | | | |
|---|---|---|---|---|
| 4,923,306 A * | 5/1990 | Fauske | ............... | G01K 17/00 165/11.1 |
| 5,319,576 A * | 6/1994 | Iannadrea | ............... | G01K 1/024 340/870.17 |
| 6,824,306 B1 * | 11/2004 | Fesmire | ............... | G01N 25/18 374/34 |
| 2014/0003460 A1 * | 1/2014 | Keyser | ............... | G01K 17/00 374/31 |
| 2016/0025661 A1 * | 1/2016 | Jossens | ............... | G21C 19/40 374/10 |

* cited by examiner

APPARATUS FOR DESTRUCTIVE EVENT TESTING OF CHEMICAL ENERGY SYSTEMS USING HIGHLY PORTABLE AND EASE OF ACCESS ADAPTIVE HEAT FLOW TESTING SYSTEMS INCLUDING REPLACEABLE AND THERMALLY ISOLATED MODULAR THERMAL SECTIONS EACH CAPABLE OF INDEPENDENT MEASUREMENTS OF A TEST ARTICLE WITH IMPROVED EASE OF TEST ARTICLE INSERTION AND REMOVAL AND RELATED METHODS

CROSS-REFERENCE TO RELATED APPLICATIONS

This application is a continuation-in-part of U.S. patent application Ser. No. 15/226,604, filed on Aug. 2, 2016, entitled "APPARATUS FOR DESTRUCTIVE EVENT TESTING OF CHEMICAL ENERGY SYSTEMS USING ADAPTIVE HEAT FLOW TESTING SYSTEMS AND RELATED METHODS," which claims priority to U.S. Provisional Patent Application Ser. No. 62/200,535, filed on Aug. 3, 2015, entitled "APPARATUS FOR DESTRUCTIVE EVENT TESTING OF CHEMICAL ENERGY SYSTEMS USING ADAPTIVE HEAT FLOW TESTING SYSTEMS AND RELATED METHODS," and is related to U.S. patent application Ser. No. 14/539,241, filed Nov. 12, 2014, entitled "ADAPTIVE HEAT FLOW CALORIMETER," which claims priority to U.S. Provisional Patent Application Ser. No. 62/035,738, filed Aug. 11, 2014, entitled "ADAPTIVE HEAT FLOW CALORIMETER," the disclosures of which are expressly incorporated by reference herein.

STATEMENT REGARDING FEDERALLY SPONSORED RESEARCH OR DEVELOPMENT

The disclosure described herein was made in the performance of official duties by employees of the Department of the Navy and may be manufactured, used and licensed by or tor the United States Government for any governmental purpose without payment of any royalties thereon. This disclosure (Navy Case 200,397) is assigned to the United States Government and is available for licensing for commercial purposes. Licensing and technical inquiries may be directed to the Technology Transfer Office, Naval Surface Warfare Center Crane, email; Cran_CTO@navy.mil.

BACKGROUND AND SUMMARY OF THE DISCLOSURE

Aspects of the present disclosure relates to performance and safely characterization or assessment systems and processes. In particular embodiments of the disclosure are directed to apparatus and methods for safety and performance characterization capable of operating before, during, and after a destructive event from a system or item under test.

Calorimetry can include processes of measuring an amount of heat released or absorbed during a chemical reaction. Calorimetry can be used in a wide range of material analysis across multiple industries. An Accelerating Rate Calorimeter (ARC) method is one method used where a material sample is placed within an oven type enclosure. Temperature within the enclosure is elevated through multiple step increases with rest periods at each step. This increase continues until the sample reaches a thermal runaway condition where the heat release of the sample can be recorded.

For battery characterization, the ARC methodology is questionable as the increasing heat may not be representative of real world conditions and may impact data collection. Lithium battery heat generation, as it approaches thermal runaway, is of interest as well as what occurs during the event.

A new approach can include use of isothermal calorimetry methodology where the cell's ambient temperature is controlled tightly during actual testing. This exemplary approach allows tor an accurate evaluation of heat generated from chemical reactions or physical changes occurring within the cell. A goal can include use of various embodiments of the disclosure to evaluate isothermal calorimetry as a potential method for characterizing the potential energy release during a destructive event, the impact to surrounding environment, and risk mitigation development.

According to an illustrative embodiment of the present disclosure, embodiments of the disclosure include exemplary processes and associated equipment to adapt or construct a heat flow calorimeter to accept a scaled pressure vessel. In some embodiments, an apparatus is provided that combines a robust sample environment of a closed bomb (to enable overcharge, burn, detonation, etc. of any sample in the closed bomb) with a highly sensitive detection capability including heat flow calorimetry. In particular, some embodiments have been constructed containing a pressure vessel in a sample chamber of the calorimeter for sample materials that would then be forced fully through decomposition. In some embodiments, an exemplary system included a pressure vessel and a capacity for deliberate overcharging of Lithium containing batteries in order to determine resulting pressure and heat energy released.

Also, efforts to obtain increased energy density of battery cells highlight a need for electrochemical techniques as well as additional characterization methods for these cells in order to meet user needs and safety requirements. In particular, a continuing need has called forth inventive efforts for developing novel calorimeters to satisfy various requirements for requiring activities including high energy density systems such as chemical energy storage systems, propellant, explosive, and pyrotechnic devices. To support optimization of electrochemical energy storage systems in particular it is necessary to understand their thermal characteristics at rest and under prescribed charge and discharge cycles. In one example, a need existed to develop a calorimeter system able to accommodate multiple battery cell configurations and provide empirical system data for use in modeling and simulation. The performance benefits from Lithium batteries are tempered by specific drawbacks, such as cost and safety being the major concerns. Lithium batteries or individual cells can experience violent behavior when subjected to abusive conditions or design flaws that can cause a destructive event. Overcharge, short circuit, and high environment temperature are just some of the conditions that can cause such events. During an event, cells can exhibit such characteristics as extreme high temperatures, deflagration, fire, and venting of electrolyte and/or toxic materials. The cell's characteristics prior to, during, and after a destructive event is important in developing preventive and mitigating hazard steps. To further understand the worst-case event produced by electrochemical cells a novel measuring system based on isothermal bomb calorimetry was developed. This system allowed for the containment of the reaction and its products while measuring the pressure and release rate of the gaseous product, as well as a complete thermal profile of the reaction. Heat flows from 0.01 to 195.42 Watts were measured with an average signal noise less than 1 mW. Moreover, these needs also included a requirement to create testing systems which are capable of larger testing capabilities that necessarily include a need to use larger systems, create more testing options with respect to samples under test, and create an ability to more cost effectively repair or replace costly components in such test systems which existing systems do not accommodate in a cost or time effective manner. As systems are scaled up in size, there is a higher level of failures in system components which require new designs to accommodate repairs or maintenance rather than throwing out large sub-assemblies. Also, there is a need to be able to swap out components for greater customized design or configurability of testing systems with respect to desired testing processes or data collection.

As an example of one embodiment, an improved measuring cell was designed and constructed to measure the heat flow of larger cells (e.g., 38 Ahr). Heat flows from 0.01 to 195.42 Watts were measured with an average signal noise less than 1 mW. This embodiment was also designed to eliminate the restrictions imposed by the stable temperature bath. By replacing the bath with a heat exchanging assembly, cost is reduced while the limits on sample size and orientation are eliminated.

Embodiments of the disclosure can include apparatus and methods for providing flexible and repairable testing capabilities for systems that generate or absorb heat such as energy storage systems. One embodiment can include a stable temperature heat exchanging assembly adapted to contain and maintain a thermally conductive fluid at a predetermined temperature, heat sinks, thermal sensor assemblies, an internal containment structure, and thermal barriers between different elements of the disclosure to isolate different sections from each other. An embodiment of the disclosure can include a system where the thermal sensor assemblies and heat sinks removeably attach to different sections of the inner containment structure so as to measure heat flow into or out of the inner containment structure's different sections without being altered by direct thermal contact with other inner containment sections. Embodiments of the disclosure permits rapid insertion/removal of samples as well as replacement of sections of an exemplary system including embodiments or parts of the thermal sensor assemblies as well as providing an ability to obtain separate thermal measurements associated with different sections of a sample under test within the inner containment structure. Other aspects of the disclosure include a capability to insert or substitute existing components such as containment structure elements, thermal sensors etc. with different sized elements or structures to accommodate different types of samples or differently sized samples under test. Embodiments can include electrical bus or wiring structures such as separate wiring sections and quick disconnects that also permit rapid repairs or alteration of configurations of various aspects of embodiments of the disclosure.

Existing systems do not provide a needed capability in a variety of areas including chemical battery testing. For example, existing systems might provide the closed bomb and low sensitivity or alternatively heat flow sensitivity but much stricter sample environment but not a combination thereof.

Additionally, existing systems are bulky, heavy, and have limited portability creating problems for ease of use. Exemplary embodiments of the present disclosure are lightweight and implement a mobile platform system to increase mobility and portability of the disclosure.

Additional features and advantages of the present disclosure will become apparent to those skilled in the art upon consideration of the following detailed description of the illustrative embodiment exemplifying the best mode of carrying out the disclosure as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the disclosure described herein are not intended to be exhaustive or to limit the disclosure to precise forms disclosed. Rather, the embodiments selected for description have been chosen to enable one skilled in the art to practice the disclosure.

Generally, one exemplary embodiment of an improved calorimeter test system has been designed to accept multiple different sizes of cylindrical lithium based battery cells. One design concern was ensuring the cells under test have access to their normal electrical test system through the use of extended charging cables and sealed instrument glands. Additional thermocouples were to be placed on and around the cells to monitor temperature at various locations inside the reaction vessel during the testing. Testing was conducted within a high energy destructive test cell. Sample cells were subjected to constant current discharge to a respective low State of Charge (SOC) for each cell. This was followed by a constant current charge to 100%, discharge again, then constant charge until the cells were no longer able to accept a current due to a failure mechanism. The charge current rates were based on the nominal charge or usage currents as identified in their manufacturer's specification sheet. During each cell evaluation, cells were placed in a closed bomb enclosure to contain any debris, fire, pressure, and/or toxic material that may be generated from a cell failure. Heat generation data was collected through isothermal calorimetry as well as typical cell characteristics of voltage, temperature, and pressure through an additional data collection system. Exemplary test systems can be designed such that each of six surfaces of an exemplary test cell (cuboid sample) can be provided a thermal conduction pathway of least resistance that can be isolated from the other five surfaces and channeled through a plurality of thermopiles. In this example, exemplary thermopiles function according to the Seebeck effect and generate a voltage corresponding to a temperature difference on either side of the precision measurement device. A plurality of thermoelectric junctions in each thermopile amplifies this effect and thus lowers a minimum temperature difference required to generate a voltage to nearly isothermal values. In addition, embodiments have been created which provide an ability to create a reconfigurable test apparatus which permits different types of test cell enclosures to be used, including a test cell enclosure receiving structure that can be used with destructive testing that can generate, e.g., heat, bursting of a test article, or an explosion in a test article with an ability to obtain test results before, during, and after a destructive test event.

Figure 1:
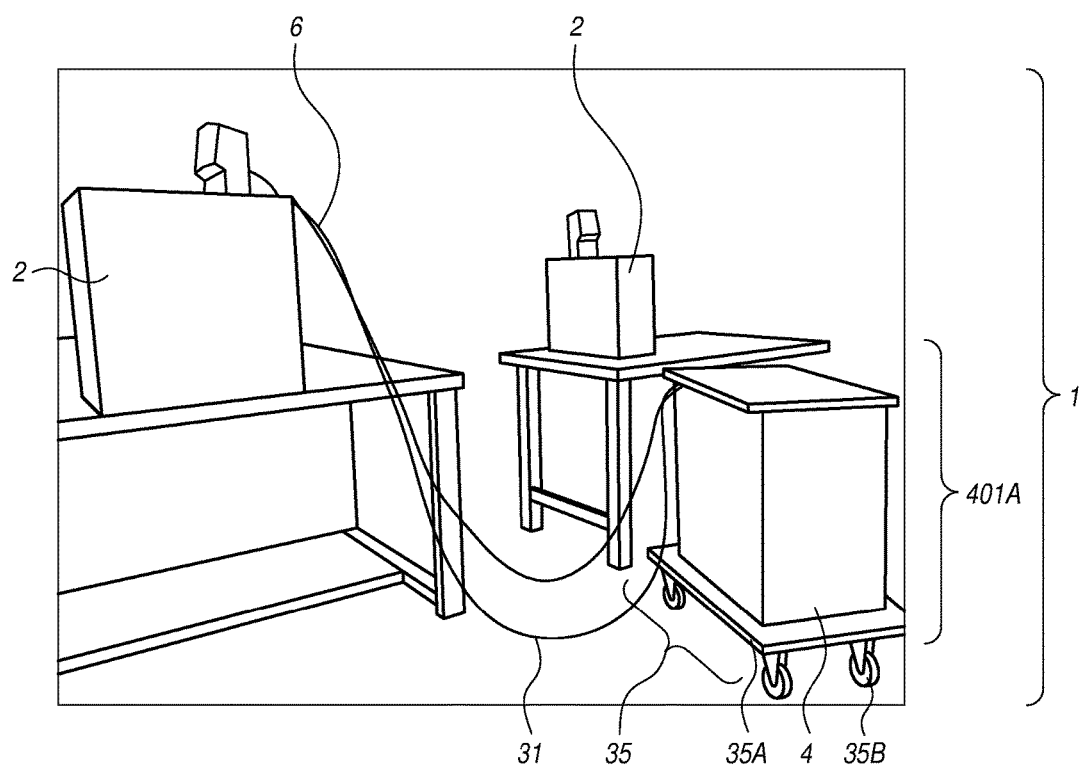
FIG. 1 is an exemplary embodiment of a calorimetric measuring unit.

FIG. 1 shows an exemplary embodiment of a calorimetric measuring unit assembly 1. The exemplary embodiment of calorimetric measuring system 1 includes thermoconductive fluid supply system (TFSS) 2, fluid transfer lines 6, thermoconductive fluid (e.g., see 11, FIG. 2), modular thermal sensor unit and removable test cell enclosure assembly (MSURTC) 401A. TFSS 2 further includes an integrated heating and cooling system (e.g., see 2A, FIG. 2) adapted to serve as an adjustable heat exchanger. A thermal isolation structure 4 is disposed over MSURTC 401A and is formed from a thermally nonconductive or inhibitive material (e.g., polyisocynate foam insulation). The thermal isolation structure 4 is used to minimize the impact of an operating environment in order to enhance the stability of the controlled temperature system. Wires 31 connect MSURTC 401A to a data acquisition system (e.g., see 25, FIG. 2). MSURTC 401A is positioned on a mobile platform 35, which includes a support structure or frame 35A and wheels 35B adapted to provide increased portability, mobility, and ease of use.

Figure 2:
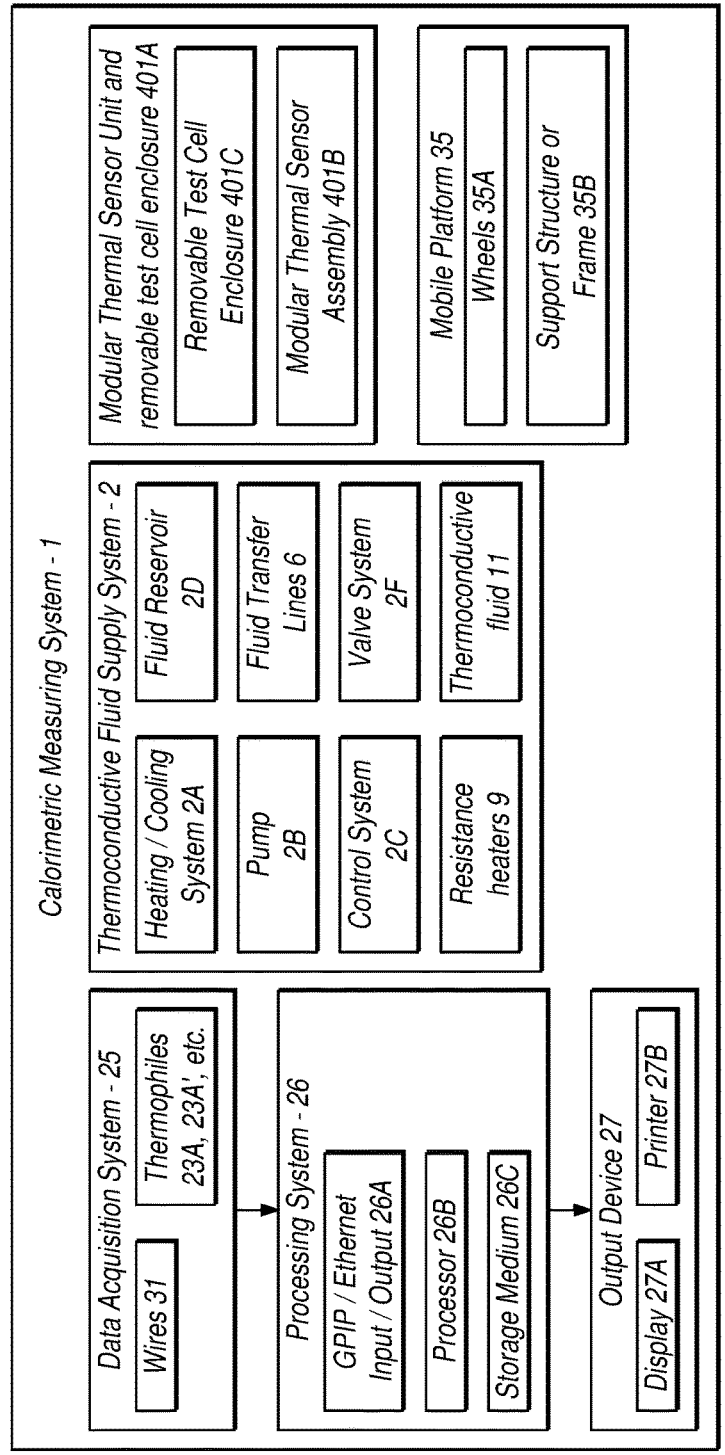
FIG. 2 is a block diagram of an exemplary calorimetric measuring unit.

FIG. 2 shows a block diagram of an exemplary calorimetric measuring system 1, as shown in e.g., FIG. 1, and includes a data acquisition system 25, a processing system 26, a output device 27, a TFSS 2, MSURTC 401A, and a mobile platform 35. Data acquisition system 25 includes wires 31 and thermopiles 23A and is connected to a processing system 26. The processing system 26 includes a GPIB/Ethernet input/output section 26A, a processor 26B, and a storage medium 26C. From the processing system 26, the measurement value is sent to an output device 27, which displays or outputs the information. In another exemplary embodiment, the output device 27 can be a display 27A or a printer 27B.

TFSS 2 is shown having heating and cooling system 2A, pump 2B, control system 2C, fluid reservoir 2D, fluid transfer lines 6, resistance heaters 9, and a valve system 2F. The MSURTC 401A further includes a modular thermal sensor assembly (MTSA) 401B and a removable test cell enclosure (RTCE) 401C. MSURTC 401C is positioned on mobile platform 35, which includes a support structure or frame 35A and wheels 35B configured to increase the portability of MSURTC 401A.

Figure 3:
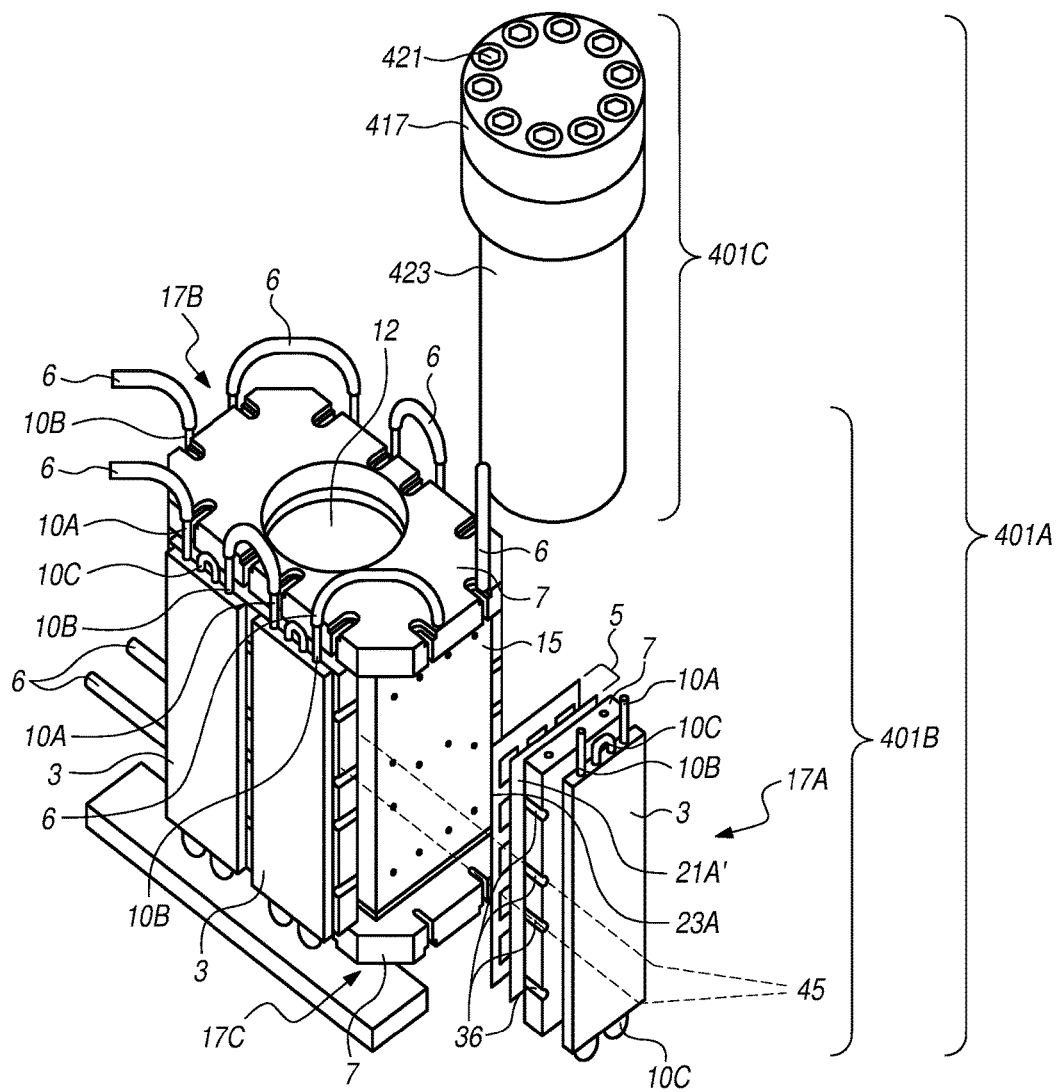
FIG. 3 is an exemplary embodiment of the disclosure showing side, top, and bottom assemblies inside the calorimetric measuring unit.

FIG. 3 shows an exemplary embodiment of the MSURTC 401A. MSURTC 401A includes the MTSA 401B and RTCE 401C. The MTSA 401B has a plurality of first modules 17A, a second module 17B, and a third module 17C. The plurality of first modules 17A can be thermally coupled to the sides of a test cell enclosure receiving structure (TCERS) 15 with non-heat conductive bolts (e.g., see 40, FIG. 6) Non-heat conductive bolts (e.g., see 40, FIG. 6) are inserted along bolt insertion axis 45 passing through recessed areas 36 located within heat sinks 7, and attach to TCERS 15. The plurality of first modules 17A can include sensor assembly 5, thermopiles 23A, thermally conductive structures 21A (rear facing thermally conductive structure omitted), 21A', heat sinks 7, and heat exchanging modules (HEM) 3. HEMs 3 are linked to one another in succession along a thermally conductive path via fluid transfer lines 6. Fluid transfer lines 6 attach the fluid supply of the TFSS (e.g., see 2, FIG. 1) to a first HEM's 3 first port 10A, where thermoconductive fluid (e.g., see 11, FIG. 2) flows into a first HEM 3, completes at least one loop 10C within HEM 3, and exits via a second port 10B where fluid transfer lines 6 connect a first HEM's 3 second port 10B to a second HEM's 3 first port 10A. This process is repeated until the plurality of first modules 17A are linked to one another in succession along a thermally conductive fluid path. On the last HEM's 3 second port 10A, the fluid transfer lines 6 connects to the input port of the TFSS 2 completing the thermally conductive fluid path. The second module 17B, is thermally coupled to the top of the TCERS 15 and includes a test cell enclosure aperture 12 and heat sink 7. The third module 17C, is coupled to the bottom of the TCERS 15 and includes heat sink 7, and fluid transfer lines 6.

Heat sinks 7, located within the plurality of first modules 17A, the second modules 17B, and the third modules 17C, can be large enough and have a high enough heat capacity such that thermal energy released through any sample (e.g., see 8, FIG. 5) is absorbed into heat sinks 7. Thermal energy absorbed by heat sinks 7 then transfers into the HEMs 3 where it is absorbed by Thermoconductive fluid 11 flowing through fluid transfer lines 6. Exemplary aspects of this disclosure as described herein also allow for calorimetric measuring assembly 1 to have an increased capacity for samples 8 that are larger and have higher heat load capacities. A high capacity of heat sink 7 can also help to maintain an isothermal operating environment.

A RTCE 401C can be removably and thermally coupled to the TCERS 15 when lowered into test cell enclosure aperture 12. The RTCE 401C includes an enclosure body 423, a lid 417, and test cell enclosure bolts 421 to couple the lid 417 to the enclosure body 423. The enclosure body 423 is formed with an internal cavity (e.g., see 405, FIG. 5) and at least one aperture (e.g., see 431, FIG. 4) leading into the internal cavity 405. Eye bolt (e.g., see 34, FIG. 4) facilitates removing, securing, and lowering of RTCE 401C into test cell enclosure aperture 12.

Figure 4:
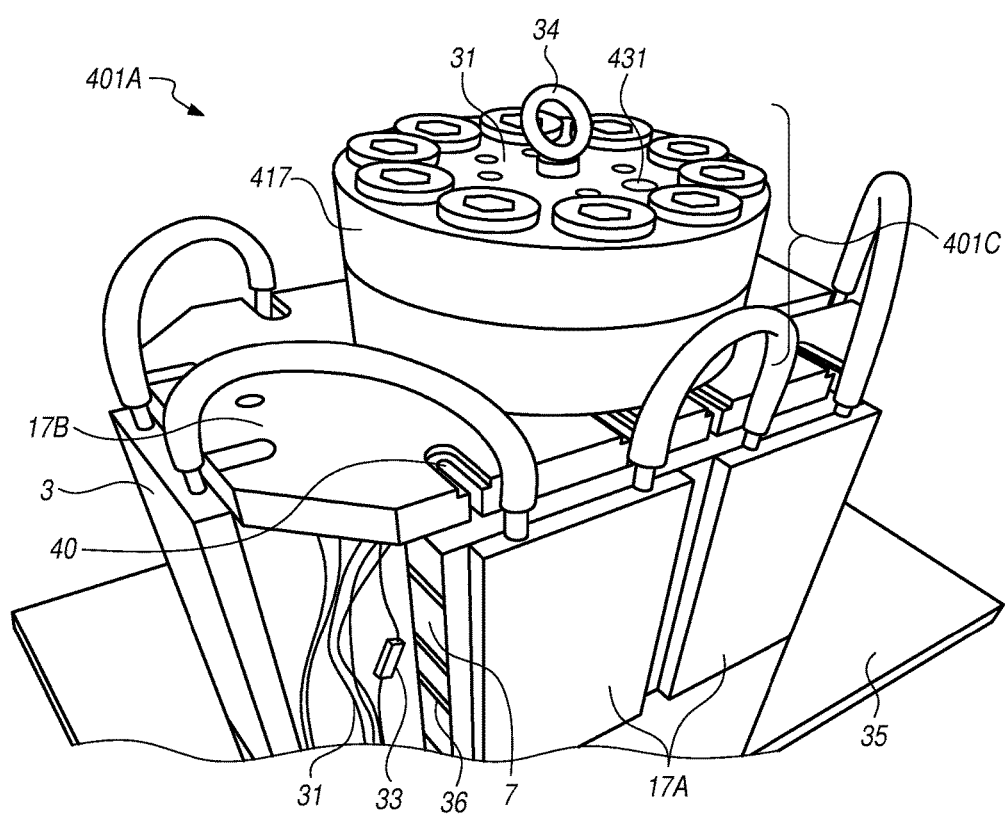
FIG. 4 is a perspective view of an assembled exemplary embodiment.

FIG. 4 shows an assembled exemplary MSURTC 401A resting on mobile platform 35 with the RTCE 401C lowered into the test cell enclosure aperture (e.g., see 12, FIG. 3) Exemplary sealing interface structures (e.g., see 426, FIG. 8) screw into apertures 431 of the lid section 417, to permit instrumentation wiring 31 to pass through the lid 417 providing pressure containment, while at the same time allowing for testing instrumentation to pass through into test cell enclosure 401C. Exemplary sealing interface structures (e.g., see 426, FIG. 8) can include a variety of test related structures such as sections that permit different types of wires 31 to pass into the RTCE 401C, which prevents gas or other elements from escaping the RTCE 401C during testing. Also, sealing interface structures (e.g., see 426, FIG. 8) can include an exhaust port, sensors such as pressure sensors, temperature sensors, etc.

The plurality of first modules 17A, second module 17B, and third module (e.g., see 17C, FIG. 3) are thermally coupled to the TCERS (e.g., see 15, FIG. 5) with non-heat conductive bolts 40. The non-heat conductive bolts 40 pass though the recessed area 36 within the heat sinks 7 and are secured into the TCERS 15. Fluid transfer lines 11 connect HEMs 3 in succession to that the thermoconductive fluid (e.g., see 11, FIG. 2) flows from the TFSS (e.g., see 2, FIG. 1), into the HEMs 3, and back into the TFSS 2.

Wiring 31 runs though wiring channels (e.g., see 30, FIG. 6) and connects a data acquisition system (e.g., see 25, FIG. 2) to sensor assemblies (e.g., see 5, FIG. 3). Wiring channels 30 are located between thermally conductive structures 21A and 21A' within sensor assemblies 5. Common plug (e.g., see 33, FIG. 7) which is connected to wiring 31 allows for wiring 31 to be quickly disconnected and reconnected to data acquisition system (e.g., see 25, FIG. 2) and various instrumentation. Eye bolt 34 facilitates the removing, securing, and lowering of RTCE 401C into test cell enclosure aperture (e.g., see 12, FIG. 3).

Figure 5:
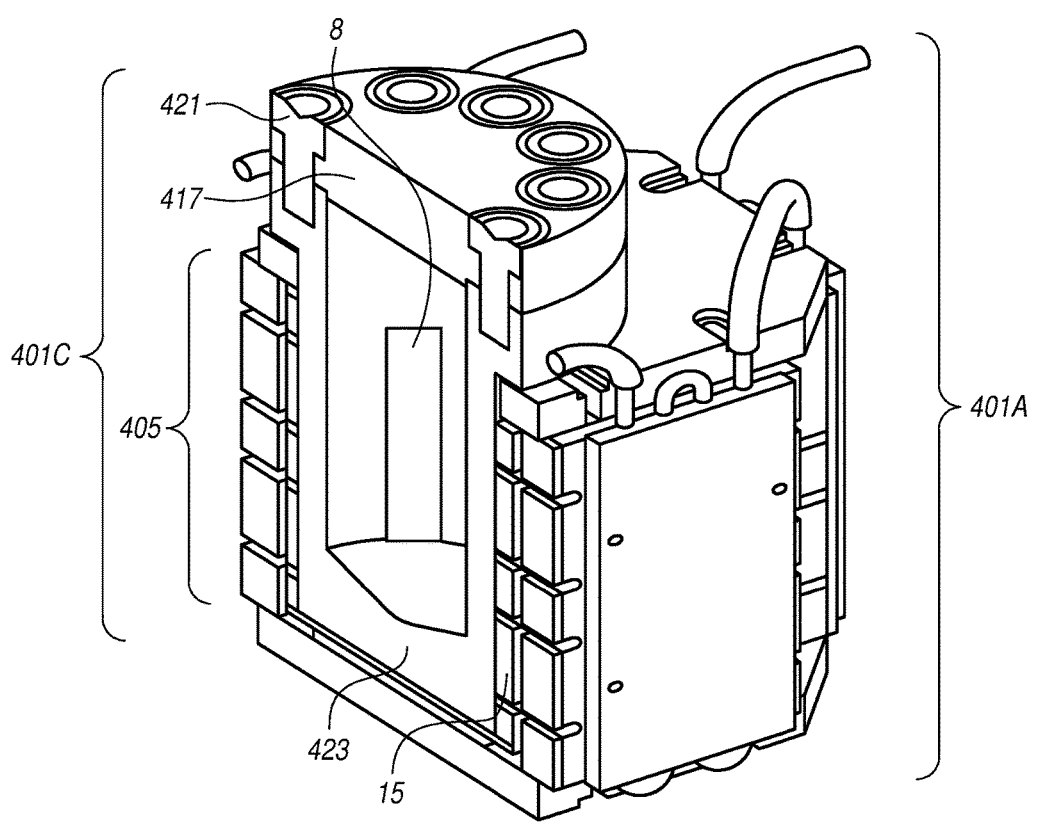
FIG. 5 is a simplified perspective drawing having some element design omitted to emphasize the fit between the sample vessel and the sample vessel receiver structure.

FIG. 5 shows a simplified view on an exemplary MSURTC 401A showing a clearance fit between the RTCE 401C and the TCERS 15 when RTCE 401C is lowered into the test cell enclosure aperture (e.g., see 12, FIG. 3). The enclosure body 423 is formed having an internal cavity 405 where sample 8 resides during testing. Test cell enclosure bolts 421 secure the lid 417 to the enclosure body 423 isolating the internal cavity 405 from the outside environment. In an alternate embodiment, an outside surface of the enclosure body (e.g., see 423, FIG. 3) can be coated with a thermal paste before being lowered into the test cell enclosure aperture 12 to facilitate heat transfer during testing.

Figure 6:
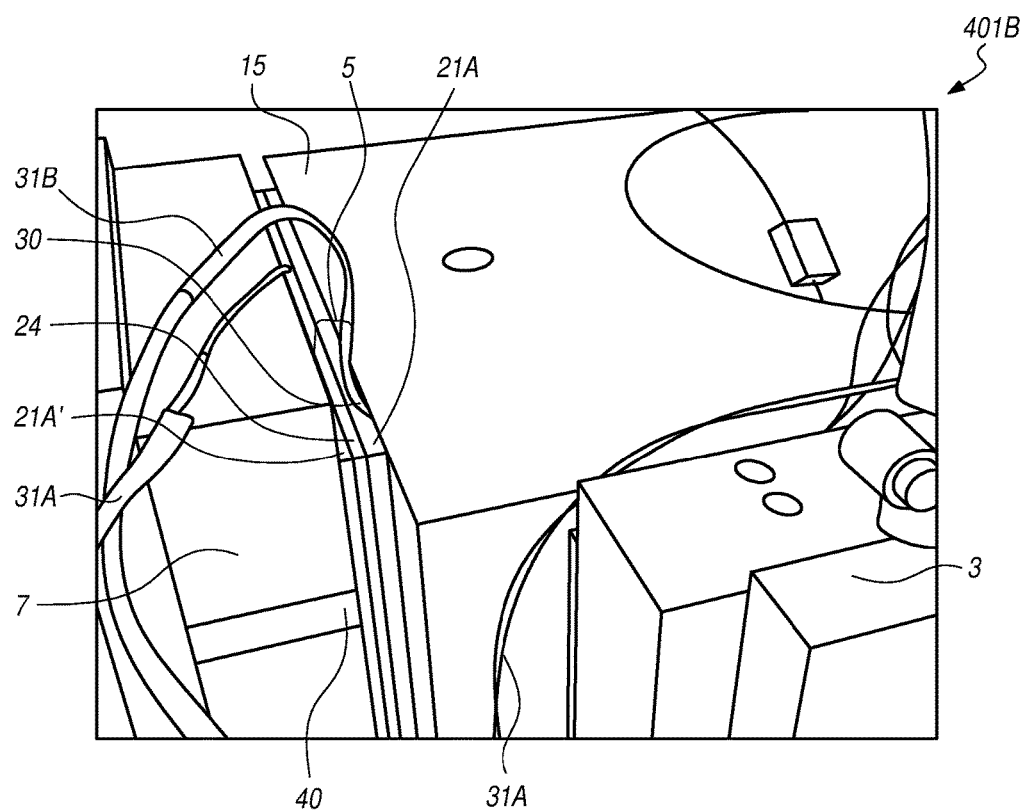
FIG. 6 is a perspective view of the exemplary embodiment showing a close up view of a sensor assembly.

FIG. 6 shows a perspective view of an exemplary MTSA 401B showing a zoomed in view of the exemplary thermal sensor assembly 5 and wires 31A and 31B. Within thermal sensor assembly 5 heat flows through thermally conductive structure 21A, thermopiles (e.g., see 23A, FIG. 3), and a second thermally conductive structure 21A'. In an exemplary embodiment, the thermopiles 23A are arranged as such to be thermally in parallel, but electrically in series. Heat sink 7 is adjacent to sensor assembly 5 and HEM 3 is located adjacent to heat sink 7. Thermally conductive structures 21A and 21A' are located on each side of sensor assembly 5 and secured to heat sink 7 and TCERS 15 with non-heat conductive bolts 40. A spacer 24 is made from a non-conductive material and operates to prevent thermopiles 23A from being damaged by a force applied to either of the thermally conductive structures 21A or 21A'. In this particular embodiment, spacer 24 is a stripe or strip that runs along the outer boarder of the thermally conductive structures 21A and 21A'. However, spacer 24 can be any shape which prevents thermopiles 23A from being damaged when a force is applied to either or both of the thermally conductive structures 21A and 21A'.

When a sample (e.g., see 8, FIG. 5) inside the TCERS 15 generates heat, such as a during a charge cycle, heat flow moves from sample 8 to the adjacent sensor assembly 5. Within sensor assembly 5, heat flows through thermally conductive structure 21A, thermopiles 23A and a second thermally conductive structure 21A'. As heat moves from thermopiles 23A to the second thermally conductive surface 21A', a measurement value is sent from thermopiles 23A to a connected data acquisition system (e.g., see 25, FIG. 2) through a first wire set 31A. Resistance heaters (e.g., see 9, FIG. 2) are supplied power by a second wire set 31B. The first and second wire sets 31A and 31B run through wiring channels 30, preventing them from being trapped or crushed between sensor assembly 5 and TCERS 15.

Figure 7:
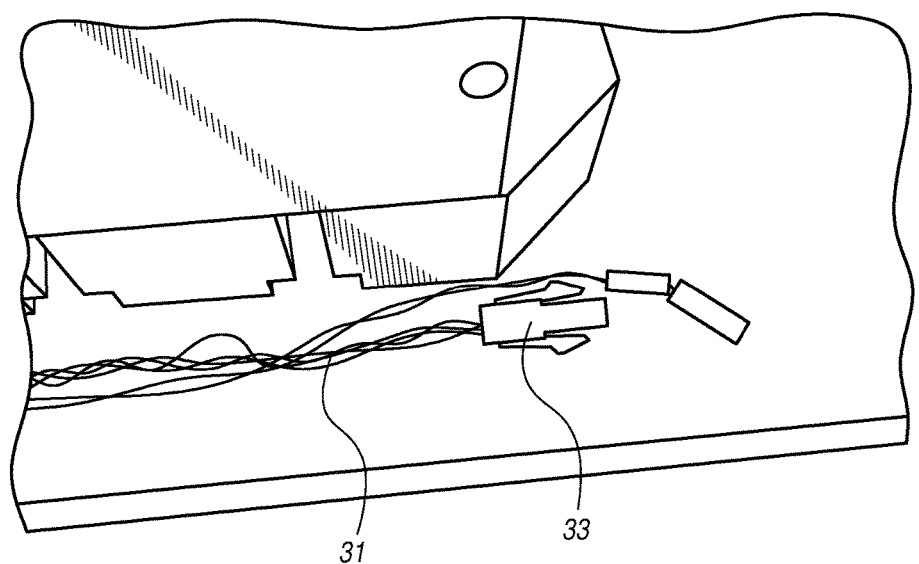
FIG. 7 is an exemplary embodiment showing wires terminating in common plugs.

Referring to FIG. 7, in an exemplary embodiment the wires 31 terminate in common plugs 33. Common plugs 33 allow for greater ease of use with the data acquisition system (e.g., see 25, FIG. 2) enabling a user to quickly disconnect the system by disconnecting common plugs 33 rather than splicing wires 31 as in prior systems.

Figure 8:
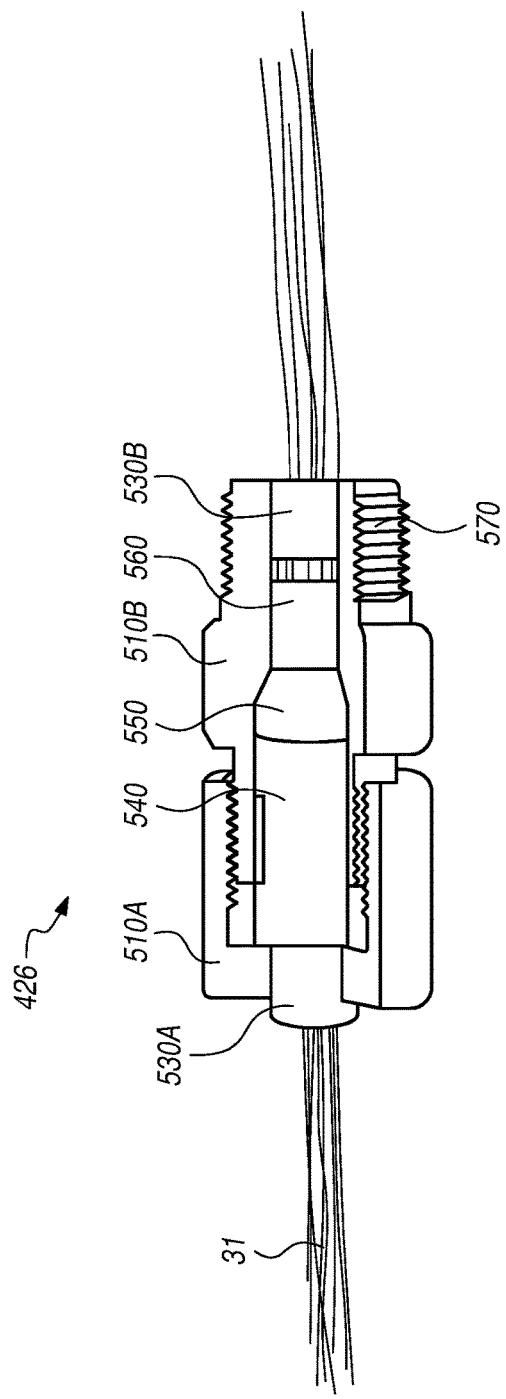
FIG. 8 shows an exemplary sealing structure.

Referring to FIG. 8, an exemplary sealing structure 426 used to allow wires 31 to pass through the lid (e.g., see 417, FIG. 3) of the RTCE (e.g., sec 401C, FIG. 3). In this example, a power lead seal structure 426 (e.g., a Conax Technologies® exemplary sealing interface structure 426) is shown with a two-part cap 510A and body 510B, which threadedly engage each other. A wire 31 passes through a center section of a cap 510A and a body 510B, which are sealed with a chemically resistant sleeve 530A, follower 540, sealant section 550, insulator 560, and another sleeve 530B, which are placed within the cap 510A and body 510B surrounding the wire(s) 31 that pass through the cap 510A and body 510B. Sealant section 550 can include a liquid or soft sealant that provides a sealing structure (e.g., when screwed together the sealant section 550 is conformed within the cap 510A and body 510B to provide a seal). The exemplary sealing interface structure 426 body 510B has threads 570 which are screwed into the lid 417. The sealing interface structure 426 is adapted to seal against gases or liquids and resists element movement through the sealing interface structure 426 under pressure.

Figure 9:
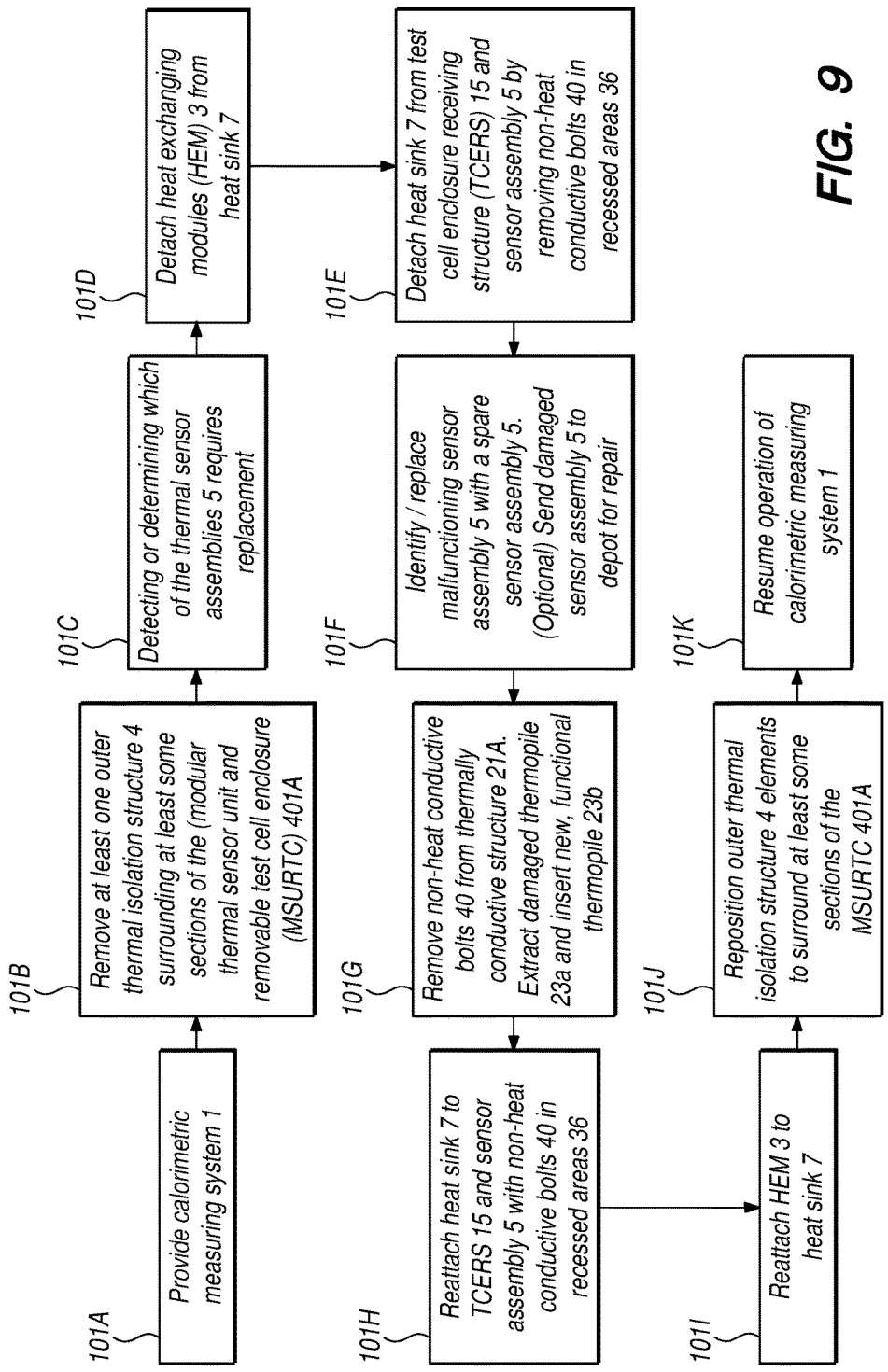
FIG. 9 is a method of repair of a system.

Referring to FIG. 9, a method of repair of a system in accordance with an embodiment of the disclosure is shown that includes providing an assembly comprising a calorimetric measuring system 1, such as described herein at step 101A. At step 101B, remove thermal isolation structure 4 surrounding at least part of the MSURTC 401A. At sept 101(C), detect or determine which of the thermal sensor assemblies 5 requires replacement. At step 101D, the HEM 3 is detached from the heat sink 7. At step 101E, heat sink 7 is detached from TCERS 15 and sensor assembly 5 by removal of non-heat conductive bolt(s) 40 in recessed areas 36. At step 101F, a malfunctioning sensor assembly 5 is identified and replaced with a spare sensor assembly 5 and the malfunctioning sensor assembly 5 is returned to the repair facility. At step 101G, non-heat conductive bolls 40 are removed from thermally conductive structure 21A. Damaged thermopile(s) 23a are extracted and new, functional thermopiles) 23b are inserted. At step 101H, heat sink 7 is reattached to TCERS 15 and sensor assembly 5 with non-heat conductive bolts 40 in recessed areas 36. At step 101I, HEM 3 is reattached to heat sink 7. At step 101J, the thermal isolation structure 4 is reattached. Operation of calorimetric measuring system 1 can resume at step 101K.

Figure 10:
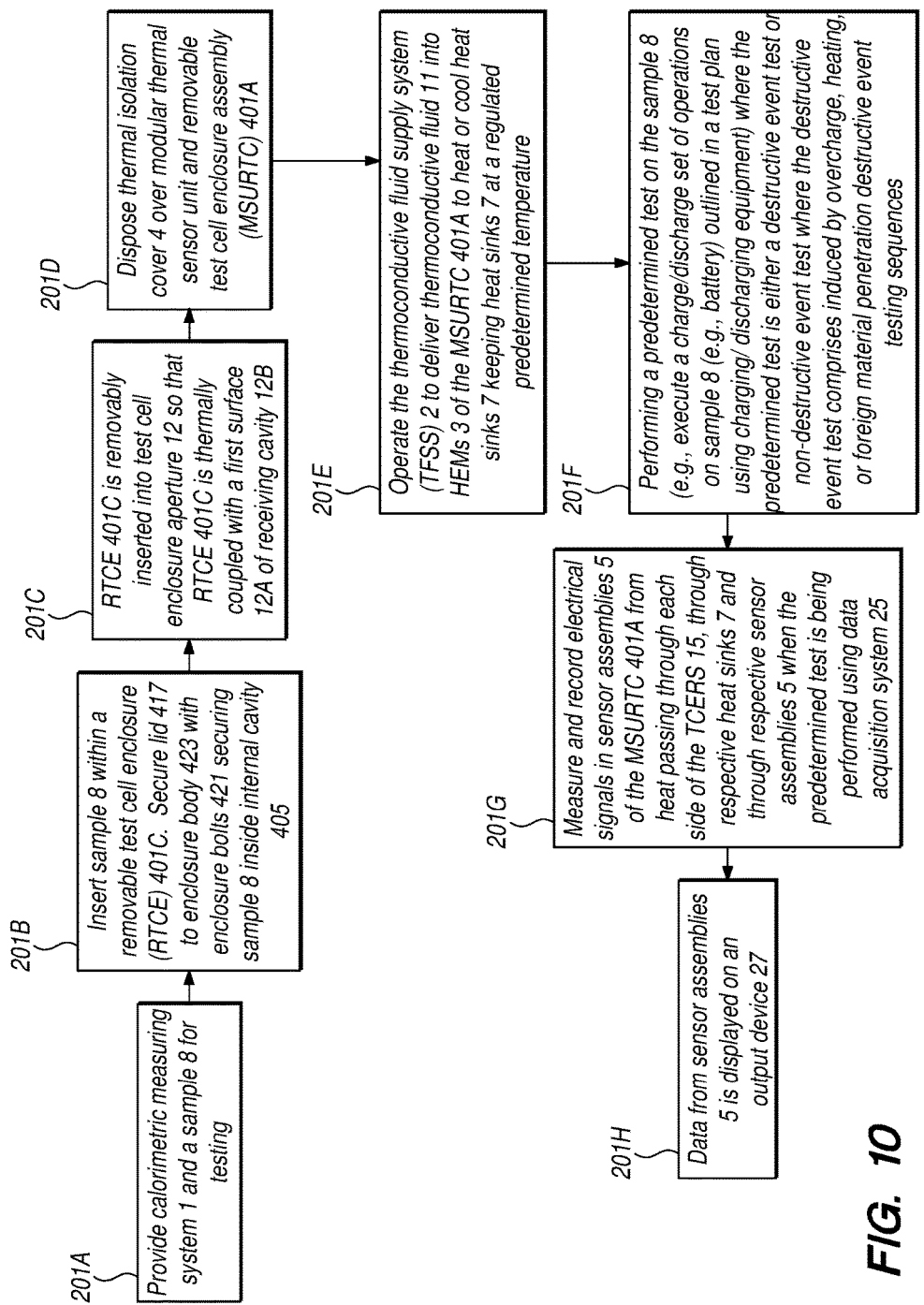
FIG. 10 is a method of use of a system in accordance with an embodiment of the disclosure.

Referring to FIG. 10, a method of use of a system in accordance with an embodiment of the disclosure can include providing calorimetric measuring system 1 and a sample 8 for testing at step 201A. At step 201B, a sample 8 is inserted within RTCE 401C. Lid 417 is secured to enclosure body 423 with enclosure bolts 421, securing sample 8 inside internal cavity 405. At step 201C, RTCE 401C is removably inserted into test cell enclosure aperture 12 so that RTCE 410C is thermally coupled with a first surface 12A of receiving cavity 12B.

At step 401D, a user disposes thermal isolation cover 4 over MSURTC 401C. At step 201E, a user operates the TFSS 2 to deliver thermoconductive fluid 11 into HEM 3 of the MSURTC 401A to heat or cool heat sinks 7, keeping heat sinks 7 at a regulated, predetermined temperature. At step 201F, a user performs a predetermined test on the sample 8 (e.g., execute a charge/discharge set of operations on sample 8 (e.g., battery) outlined in a test plans using charge/discharging equipment. The predetermined test is either a destructive event test or non-destructive event test where the destructive event test comprises induced overcharging, heating, or foreign material penetration destructive event test sequences.

At sept 201G, a user measures and records electrical signals in sensor assemblies 5 of the MSURTC 401A from heat passing through each side of the TCERS 15, through respective heat sinks 7, and through respective sensor assemblies 5 when the predetermined test is being performed using data acquisition system 25. At step 201H, data from sensor assemblies 5, is displayed on an output device 27.

Figure 11:
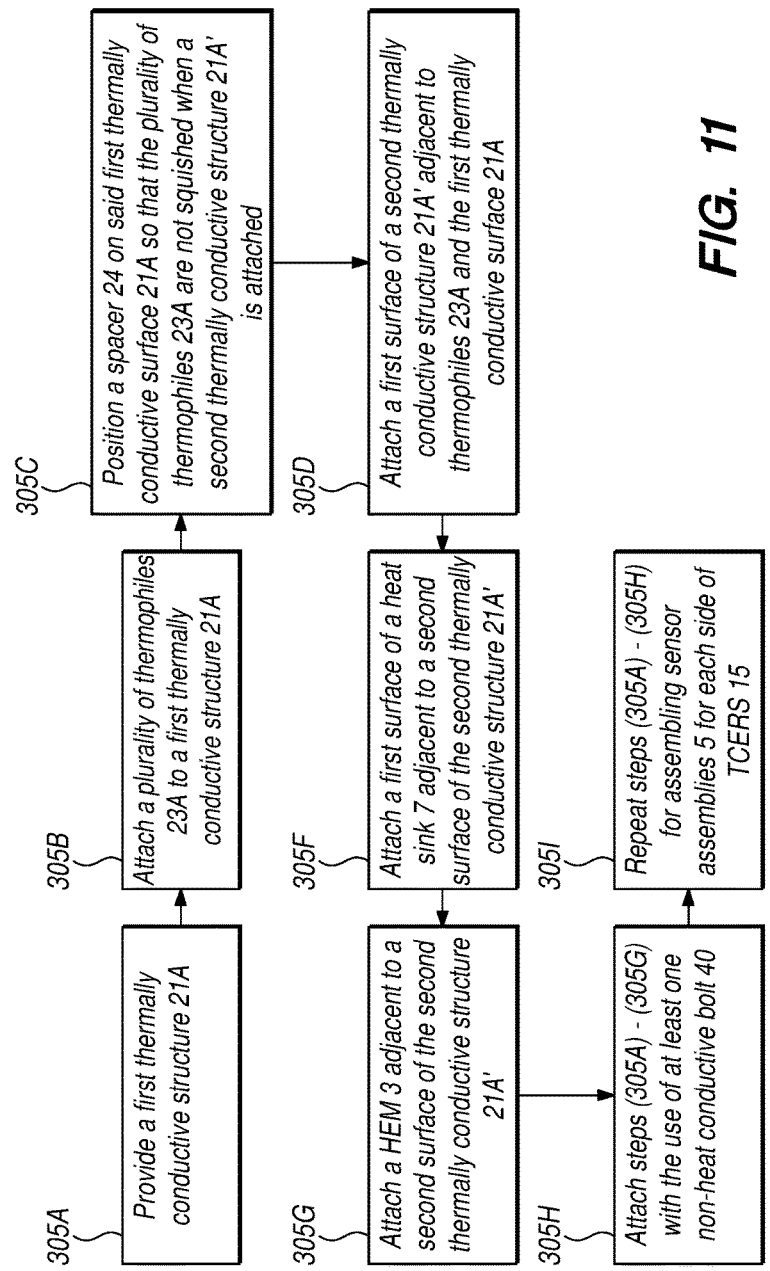
FIG. 11 is an exemplary method of manufacture of a sensor assembly.

Referring to FIG. 11, an exemplary method of manufacture of a sensor assembly 5 includes providing a first thermally conductive structure 21A at step 305A. At step 305B, a plurality of thermopiles 23A are attached to first thermally conductive structure 21A. In one embodiment, thermopiles 23A are adhered to first thermally conductive structure 21A with a thermally conductive paste, improving thermal contact and providing a weak adhesive bond. At step 305C, positioning a spacer 24 on the first thermally conductive surface 21A so that the plurality of thermopiles 23A are not crushed and thereby damaged by excessive compression when a second thermally conductive structure 21A' is attached and non-heat conductive bolts 40 are tightened. At step 305D, attach a first surface of the second thermally conductive structure 21A' adjacent to thermopiles 23A, and the first thermally conductive structure 21A. At step 305F, attach a first surface of a heat sink 7 adjacent to a second surface of the second thermally conductive structure 21A'. At step 305G, attach a HEM 3 adjacent to a second surface of the second thermally conductive structure 21A'. At step 305H, attaching steps (305A)-(305G) with the use of at least one non-heat conductive bolt 40. At step 305I, repeating steps (305A)-(305H) for assembling sensor assemblies 5 for each side of TCERS Although the disclosure has been described in detail with reference to certain preferred embodiments, variations and modifications exist within the spirit and scope of the disclosure as described and defined in the following claims.

The invention claimed is:

1. A testing system comprising:
   a test data acquisition and control system comprising a data acquisition system, a processing system, and an output device;
   a thermoconductive fluid supply system comprising a pump, a heating section, a cooling section, a temperature control section, and a thermoconductive fluid supply and fluid delivery section, wherein said thermoconductive fluid supply system is adapted to accept or donate thermal energy;
   a modular thermal sensor assembly comprising a body formed with a receiving cavity and a plurality of first modules, a second module, and a third module, wherein the plurality of said first modules are thermally coupled with a first plurality of sides of said body and said second and third modules are thermally coupled with a second plurality of sides of said body;
   a removable test cell enclosure, which is removably inserted and thermally coupled with side walls of said receiving cavity, comprising an enclosure body, a lid, and coupling structures for coupling the lid to said enclosure body, wherein said enclosure body is formed with an internal cavity and an aperture leading into said enclosure body, said lid comprising a plurality of apertures formed to receive said coupling structures and a lift system attaching structure;
   a thermal isolation structure disposed around at least a first, a second, and a third side of a modular thermal sensor assembly and removable test cell enclosure system (MTSARTCES), wherein said MTSARTCES comprises said modular thermal sensor assembly and said removable test cell enclosure; and
   a mobile platform comprising a plurality wheels and a support structure or frame, wherein said MTSARTCES is coupled to said mobile platform;
   wherein said data acquisition system comprises wires and said thermal sensors;
   wherein said processing system comprises an input/output section, a processor, and a storage medium;
   wherein each of said first modules comprises a thermal sensor assembly comprising a first side plate, a second side plate, a plurality of thermal sensors disposed between said first and second side plates, and a thermally insulative spacer disposed around edges of facing sides of said first and second side plates formed with a thickness at least that of said thermal sensors, said first modules each further comprising a removable heat sink that is thermally coupled with one of said first or second side plates, a heat exchange module formed with a fluid manifold section coupled to said fluid delivery section and is adapted for receiving and passing said thermoconductive fluid through said heat exchange module, wherein said first modules are coupled together with non-heat conductive bolts, wherein said first and second side plates are shaped such that they are coextensive with said first plurality of sides of said body.

2. The testing system of claim 1, wherein said heat exchange system further comprises a controlled fluid reservoir with a stirrer or pump operable to circulate said thermoconductive fluid to facilitate a desired temperature of said thermoconductive fluid.

3. The testing system of claim 1, wherein each of said thermal sensor assemblies output separate measurement data to measure heat flow from respective faces of said sample oriented towards a respective wall section facing said sample, wherein said thermal sensors comprise thermopiles arranged as parallel thermal pathways and electrically connected in series to sum and amplify a generated signal from said thermopiles.

4. The testing system of claim 1, wherein said thermal sensor assemblies are configured to output separate measurements to independently measure heat flow from each side of said removable test cell enclosure, wherein said thermal sensor assemblies comprise thermopiles arranged as parallel thermal pathways, but electrically connected in series to sum and amplify a generated signal from said thermopiles.

5. The testing system of claim 1, wherein at least one thermal sensor assembly further comprises one or more non-heat conductive bolts or couplers that goes through said first and second heat sink wall sections and attaching to said removable test cell enclosure so as to thermally couple said at least one thermal sensor assembly to said removable test cell enclosure.

6. The testing system of claim 1, wherein said output device is a printer or a display.

7. A method of repair of a testing system and assembly comprising:
   providing a testing system comprising:
      a test data acquisition and control system comprising a data acquisition system, a processing system, and an output device;

a thermoconductive fluid supply system comprising a pump, a heating section, a cooling section, a temperature control section, and a thermoconductive fluid supply and fluid delivery section, wherein said thermoconductive fluid supply system is adapted to accept or donate thermal energy;

a modular thermal sensor assembly comprising a body formed with a receiving cavity and a plurality of first modules, a second module, and a third module, wherein the plurality of said first modules are thermally coupled with a first plurality of sides of said body and said second and third modules are thermally coupled with a second plurality of sides of said body;

a removable test cell enclosure, which is removably inserted and thermally coupled with side walls of said receiving cavity comprising an enclosure body, a lid, and coupling structures for coupling the lid to said enclosure body, wherein said enclosure body is formed with an internal cavity and an aperture leading into said enclosure body, said lid comprising a plurality of apertures formed to receive said coupling structures and a lift system attaching structure;

a thermal isolation structure disposed around at least a first, a second, and a third side of a modular thermal sensor assembly and removable test cell enclosure system (MTSARTCES), wherein said MTSARTCES comprises said modular thermal sensor assembly and said removable test cell enclosure; and a mobile platform comprising a plurality wheels and a support structure or frame, wherein said MTSARTCES is coupled to said mobile platform;

wherein said data acquisition system comprises wires and said thermal sensors;

wherein said processing system comprises an input/output section, a processor, and a storage medium;

wherein each of said first modules comprises a thermal sensor assembly comprising a first side plate, a second side plate, a plurality of thermal sensors disposed between said first and second side plates, and a thermally insulative spacer disposed around edges of facing sides of said first and second side plates formed with a thickness at least that of said thermal sensors, said first modules each further comprising a removable heat sink that is thermally coupled with one of said first or second side plates, a heat exchange module formed with a fluid manifold section coupled to said fluid delivery section and is adapted for receiving and passing said thermoconductive fluid through said heat exchange module, wherein said first modules are coupled together with non-heat conductive bolts, wherein said first and second side plates are shaped such that they are coextensive with said first plurality of sides of said body;

commencing a repair operation comprising:

removing said thermal isolation structure from said modular thermal sensor unit and removable test cell enclosure system;

detecting or determining which of said thermal sensor assemblies requires replacement;

detaching said heat exchanging modules from said heat sink of a malfunctioning thermal sensor assembly;

removing one or more said non-heat conductive bolts from said first modules and detaching one of said removable heat sinks coupled to said side plates;

replacing one of said malfunctioning thermal sensor assemblies within said first side plate with a replacement thermal sensor assembly including at least one new said thermal sensors;

placing said first side plate with said replacement thermal sensor assembly in contact with one of said heat sinks formerly in contact with said first side plate;

placing one of said heat sinks formerly in contact with said first side plate in contact with said replacement thermal sensor assembly;

attaching heat exchanging modules from said heat sinks formally in contact with said first place;

reinserting one or more said non-heat conductive bolts into said first side plate of said replacement thermal assembly and securing one or more said non-heat conductive bolts;

replacing the thermal isolation structure over said modular thermal sensor unit and removable test cell enclosure system.

8. A method as in claim 7, further comprising the commencing of testing after said repair operation is completed.

9. A method as in claim 7, wherein at least one of said thermal sensors is a thermopile.

10. A method as in claim 7, wherein said malfunctioning thermal sensor assemblies are sent to a repair facility for repair.

11. A method of using a testing system comprising:

providing a sample, wherein said sample is inserted in an internal cavity within a removable test cell enclosure;

coupling a lid of said removable test cell enclosure to an enclosure body sealing said sample within said internal cavity;

removably inserting said removable test cell enclosure into a receiving cavity and thermally coupling said removable test cell enclosure with a first surface of said receiving cavity;

placing a thermal isolation structure surrounding at least a first, second, and third sides of a modular thermal sensor unit and test cell enclosure system;

operating a thermoconductive fluid supply system to deliver a thermoconductive fluid into heat exchanging modules to heat or cool heat sinks keeping heat sinks at a regulated temperature;

charging or discharging a sample as outlined in a test plan, wherein said test plan is determined by an operator or established protocol;

measuring and recording data of heat flow from said sample through each side of said test cell enclosure receiving structure independently of the other sides of said test cell enclosure receiving structure; and displaying said data of heat flow on an output device.

12. A method as in claim 11, wherein said charging and discharging according to said test plan results termination in a destructive event, wherein said destructive event is induced by overcharge, heating, or foreign material penetration.

13. A method as in claim 11, wherein the number of times said sample is charged and discharged is variable from zero to any number directed by said sample and/or test plan.

14. A method as in claim 11, wherein charge and discharge rates can be variable or constant as required by said sample and/or test plan.

15. A method as in claim 11, further comprising the step of interpreting said data of heat flow after displaying said data of heat flow.

* * * * *